(12) United States Patent
Takino et al.

(10) Patent No.: US 10,813,795 B2
(45) Date of Patent: Oct. 27, 2020

(54) DISPOSABLE ABSORBENT WEARING ARTICLE

(71) Applicant: Unicharm Corporation, Shikokuchuo-shi, Ehime (JP)

(72) Inventors: Shunsuke Takino, Kanonji (JP); Hideaki Maki, Kanonji (JP); Katsufumi Aoki, Kanonji (JP); Takuya Inoue, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 369 days.

(21) Appl. No.: 15/740,855

(22) PCT Filed: May 19, 2016

(86) PCT No.: PCT/JP2016/064842
§ 371 (c)(1),
(2) Date: Dec. 29, 2017

(87) PCT Pub. No.: WO2017/002479
PCT Pub. Date: Jan. 5, 2017

(65) Prior Publication Data
US 2018/0193206 A1    Jul. 12, 2018

(30) Foreign Application Priority Data
Jun. 30, 2015  (JP) ................. 2015-132229

(51) Int. Cl.
*A61F 13/15*   (2006.01)
*A61F 13/49*   (2006.01)
*A61F 13/496*  (2006.01)

(52) U.S. Cl.
CPC ...... *A61F 13/49011* (2013.01); *A61F 13/496* (2013.01); *A61F 13/49017* (2013.01); *A61F 13/49019* (2013.01); *A61F 13/49061* (2013.01)

(58) Field of Classification Search
CPC .......... A61F 13/49011; A61F 13/49017; A61F 13/49019; A61F 13/49061; A61F 13/496
(Continued)

(56) References Cited

U.S. PATENT DOCUMENTS 6,280,426 B1 *  8/2001  Turner ............ A61F 13/49466
                                               604/385.01
6,425,889 B1    7/2002  Kitaoka et al.
(Continued)

FOREIGN PATENT DOCUMENTS

JP       4-32718 U      3/1992
JP     2000-140004 A    5/2000
(Continued)

OTHER PUBLICATIONS

International Search Report in PCT/JP2016/064842, dated Jun. 14, 2016, 4pp.

*Primary Examiner* — Jacqueline F Stephens
(74) *Attorney, Agent, or Firm* — Hauptman Ham, LLP

(57) ABSTRACT

Disclosed is a disposable absorbent wearing article with a given part curved to protrude outward. At least one waist region, which is at least one of front and rear waist regions in a disposable absorbent wearing article such as a pull-on diaper includes an elastic band that form a part of a skin-facing surface and extends in a lateral direction. The elastic band has a middle part in the lateral direction elastically contracting, with an elastic contraction amount of the middle part being larger than a component part of article facing the middle part without being joined to the middle part, in a thickness direction of the middle part in the lateral direction. An absorbent core material in the at least one waist region has a deformation guide extending in a direction crossing the elastic band, formed to facilitate forming of a bulging part in the wearing article.

14 Claims, 12 Drawing Sheets

(58) Field of Classification Search
USPC .......... 604/385.201, 385.17, 385.24, 385.27,
604/385.29, 385.3, 385.26
See application file for complete search history.

(56) References Cited

U.S. PATENT DOCUMENTS

2011/0066127 A1\* 3/2011 Kuwano ........... A61F 13/49001
604/385.3
2013/0041340 A1 2/2013 Kawakami et al.

FOREIGN PATENT DOCUMENTS

| JP | 2000-288016 A | 10/2000 |
|---|---|---|
| JP | 2011-240054 A | 12/2011 |
| JP | 2015-62616 A | 4/2015 |
| JP | 2015-93168 A | 5/2015 |
| WO | 2015/072218 A1 | 5/2015 |

\* cited by examiner

DISPOSABLE ABSORBENT WEARING ARTICLE

RELATED APPLICATIONS

The present application is a National Phase of International Application Number PCT/JP2016/064842, filed May 19, 2016, which claims priority to Japanese Application Number 2015-132229, filed Jun. 30, 2015.

TECHNICAL FIELD

The present disclosure relates to a disposable absorbent wearing article such as a disposable diaper.

BACKGROUND ART

Conventionally, disposable absorbent wearing articles such as a disposable diaper includes a front waist region, a rear waist region and a crotch region positioned between the front and the rear waist regions wherein an absorbent structure extends over the crotch region and the front and the rear waist regions, and at least either one of the front and the rear waist regions and the crotch region is curved outward when an elastic member is contracted. For example, an absorbent article disclosed in Patent Literature 1 includes an elongated absorbent chassis having a waist region and a crotch region. The article has both side edges extending in a vertical direction, and both upper and lower ends extending in a lateral direction, provided with barrier flaps with which elastic members are attached. The absorbent chassis assumes a cup-like shape when the elastic members of the barrier flaps are contracted.

CITATION LIST

Patent Literature

PTL 1: Japanese Unexamined Patent Application Publication No. 2000-288016 (JP2000-288016A)

SUMMARY OF INVENTION

Technical Problem

Conventional absorbent articles provided with barrier flaps and making the absorbent structure of the absorbent articles curve makes the absorbent chassis as a whole curve to be in a cup-like shape to be space apart from the skin of a wearer with the barrier flaps being in contact with the skin of the wearer. Thus, a consistent cup-shape is difficult to achieve with the absorbent chassis in the worn state of the article. Such a wearing article gives a bulky impression and thus is not preferable in appearance. Furthermore, body exudates may flow on the inner side of the absorbent chassis in the cup-like shape to soil the skin of the wearer over a wide area.

An object of the present invention is to provide an improved disposable absorbent wearing article such as a disposable diaper having a given part in front and rear waist regions and a crotch region curved to protrude outward so that a space that may contain body exudates is formed on the inner side of the wearing article.

Solution to Problem

The present invention for solving the problems described above is directed to a disposable absorbent wearing article having an upper and lower direction and a lateral direction crossing each other in a worn state of the article, the article including a front waist region defined by a front waist panel, a rear waist region defined by a rear waist panel and a crotch region positioned between the front and rear waist regions and defined by a crotch panel. The front waist region, the rear waist region and the crotch region each have a skin-facing surface and a clothing-facing surface respectively facing the skin and clothing of a wearer. An absorbent structure including an absorbent core material extends to the front and the rear waist regions centering on the crotch region.

In the disposable absorbent wearing article according to the present invention, at least one waist region of the front and the rear waist regions includes an elastic band forming a part of the skin-facing surface and has a middle part in the lateral direction and elastically contracted in the lateral direction. In the at least one waist region, an elastic contraction amount in the middle part of the elastic band in the lateral direction is larger than an elastic contraction amount of a component part of the article facing the middle part without being joined to the middle part in a thickness direction of the middle part in the lateral direction. In the core material in the at least one waist region, a deformation guide is formed that extends in a direction to cross the elastic band and facilitates curving of the core material in the lateral direction.

The present invention includes at least the following embodiments, which may be taken in isolation or in combination.

(1) The elastic band is formed of an elastic strip having both side parts in the lateral direction joined to the at least one waist region and having at least a lower part of the middle part not joined to the at least one waist region.

(2) The at least one waist region includes an outer sheet defining the clothing-facing surface, an inner sheet defining the skin-facing surface, and an elastic member provided between the outer sheet and the inner sheet and stretched in the lateral direction.

(3) In the at least one waist region, a non-elastic region is formed in the component part of the article facing the middle part.

(4) The at least one waist region includes a waist elastic area extending along a top edge of the waist region and elastically contractible in the lateral direction, and has a part positioned more on a lower side than the waist elastic area folded in the upper and lower direction in an overlapping manner so that a Z-shaped folded part is formed. In the Z-shaped folded part, both side parts positioned on both sides in the lateral direction are folded in an overlapping manner and joined to each other, a part between both side parts is in a non-joined state, and a part of the waist elastic area forms the elastic band.

(5) The deformation guide is at a position overlapping the elastic band in planary view of the diaper.

(6) The deformation guide is at a position not overlapping with the elastic band in planary view of the diaper.

(7) The elastic band is formed of a nonwoven fabric including elastic yarns, and the nonwoven fabric is elastically stretched in the lateral direction at least in the middle part of the elastic band.

(8) The elastic band is formed of a nonwoven fabric to which string-like or strip elastic member linearly extending in the lateral direction is contractibly attached.

(9) A plurality of string-like or string-like elastic members linearly extending in the lateral direction are contractibly attached to the at least one waist region while being arranged side by side along the upper and lower direction. The plurality of elastic members include an elastic member having an inner end facing a vertical center line dividing equally a length of the diaper in the lateral direction.

(10) A length of a distance between the vertical center line and the inner end of at least one of the plurality of elastic members positioned in a lowermost part in the upper and lower direction is smaller than a length of a distance between the vertical center line and the inner end of one of the elastic members positioned more on an upper side than the at least one elastic member.

(11) The deformation guide is at least one slit or groove formed in the core material of the crotch panel extending in the upper and lower direction.

(12) The slit includes a slit positioned on a vertical center line dividing equally a length of the wearing article in the lateral direction and slits symmetrically formed about the vertical center line.

(13) The slit has both ends in the upper and lower direction formed in at least one of a part between a front edge of the core material and a lateral center line of the wearing material and a part between a rear edge of the core material and the lateral center line.

(14) The core material has at least one of a thickness and a density varying between parts adjacent to the deformation guide in the lateral direction and the deformation guide.

Advantageous Effects of Invention

A disposable absorbent wearing article according to one or more embodiments of the present invention has at least one of front and rear waist regions curved to protrude outward from the wearing article together with a core material at a part where a deformation guide is formed when an elastic band is elastically contracted in a lateral direction. A space into which body exudates may flow may be formed between the part where the deformation guide is formed and the skin of a wearer.

BRIEF DESCRIPTION OF DRAWINGS

The drawings illustrate specific embodiments of the present invention including optional and preferred embodiments as well as essential features of the invention.

DESCRIPTION OF EMBODIMENTS

The embodiments described below relates to a diaper as illustrated in FIGS. 1 through 12, including both optional and preferred features as well as those features that are essential features of the present invention.

Figure 1A:
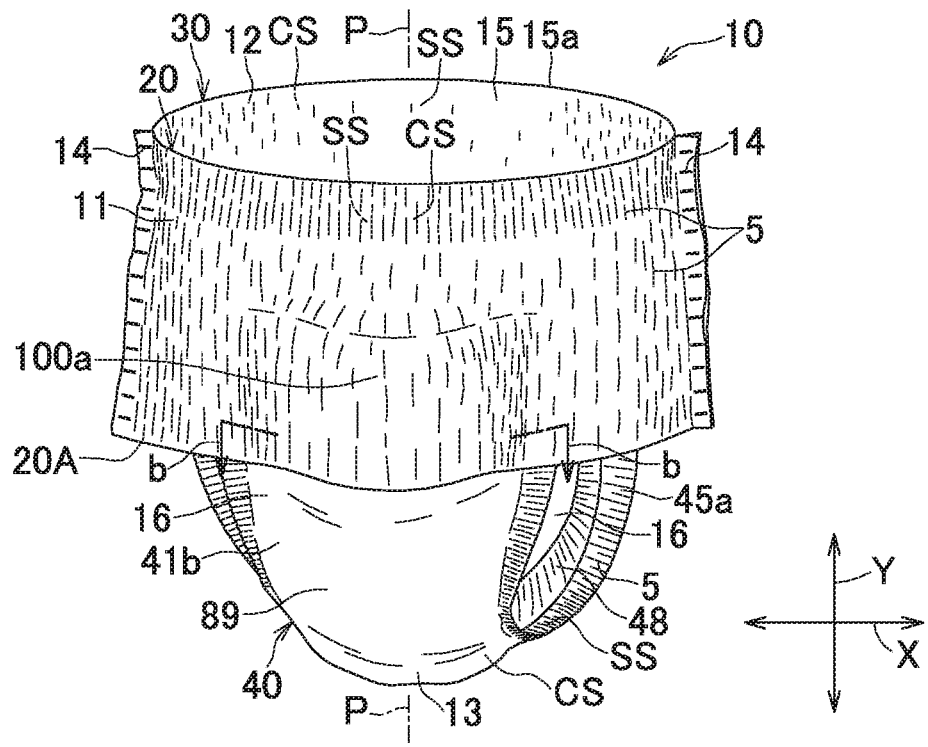
FIG. 1A is a front view of a disposable diaper that is a disposable absorbent wearing article according to the present invention in a worn state.
Figure 1B:
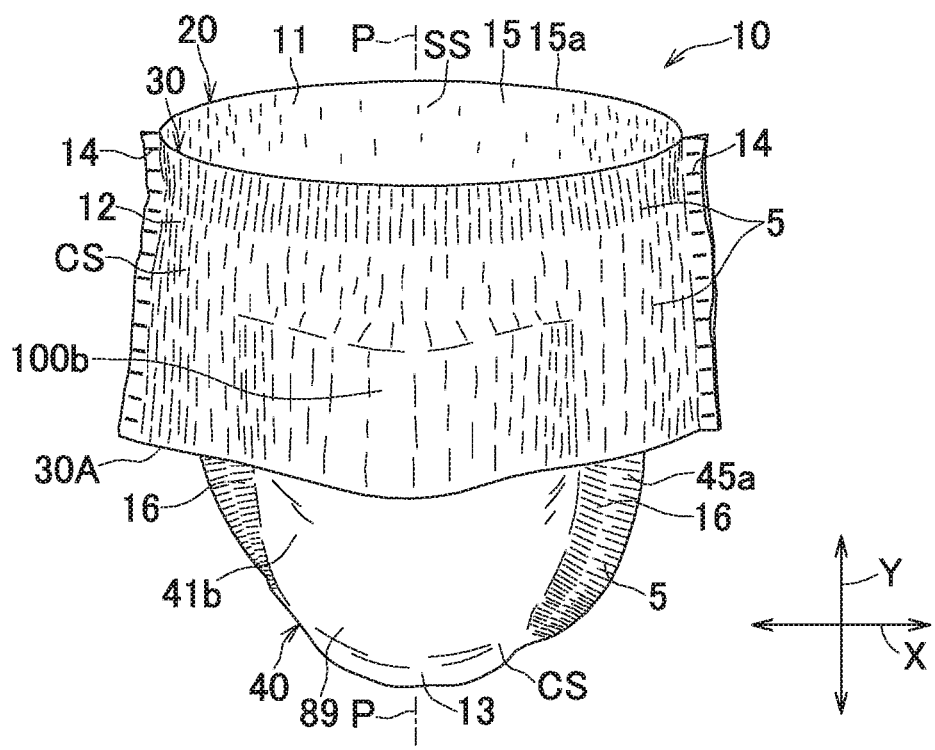
FIG. 1B is a rear view of the diaper.

FIG. 1 is a diagram illustrating a shape of a pull-on diaper 10 which is one example of a disposable absorbent wearing article according to the present invention in a worn state of the article. FIG. 1A is a front view of the diaper 10. FIG. 1B is a rear view of the diaper 10. A wearer is omitted in these figures. The diaper 10 illustrated in FIG. 1 has a vertical direction Y, a lateral direction X crossing the vertical direction Y, and a vertical center line P extending in the vertical direction Y and dividing equally the length in the lateral direction X. The diaper 10 has a symmetrical shape relative to the vertical center line P. In the present invention, the vertical direction Y is also referred to an upper and lower direction. The diaper 10 may include a front waist panel 20 defining a front waist region 11, a rear waist panel 30 defining a rear waist region 12, and a crotch panel 40 defining a crotch region 13. The front and the rear waist panels 20 and 30 have both side edges joined to each other at seams 14 and define a waist opening 15. The crotch panel 40 is joined to the front and the rear waist panels 20 and 30. A pair of leg openings 16 is defined by the crotch panel 40 and the front and the rear waist panels 20 and 30. The front and the rear waist panels 20 and 30 and the crotch panel 40 each may include a skin-facing surface SS (see FIG. 2) and a clothing-facing surface CS (described late) respectively facing the skin and the clothing of the wearer except for such as a diaper. The clothing (or non-skin)-facing surface CS respectively facing the skin and the clothing of a wearer except for the diaper. The clothing-facing surface CB is formed with multiple gathers 5. The pull-on diaper 10 according to the present invention is what has the waist opening 15 and the leg openings 16 respectively preformed and is worn by inserting both legs in the leg openings 16 and pulling up the diaper 10 to the wearer's waist. The diaper 10 of this type is also known as a pant diaper.

The front waist panel 20 of the diaper 10 illustrated in FIG. 1A has a bulging part 100a protruding outward from the diaper 10 formed over the vertical center line P. Similarly, the rear waist panel 30 illustrated in FIG. 1B also has a bulging part 100b protruding outward from the diaper 10 (see FIG. 6). The bulging parts 100a and 100b are described later.

Figure 2:
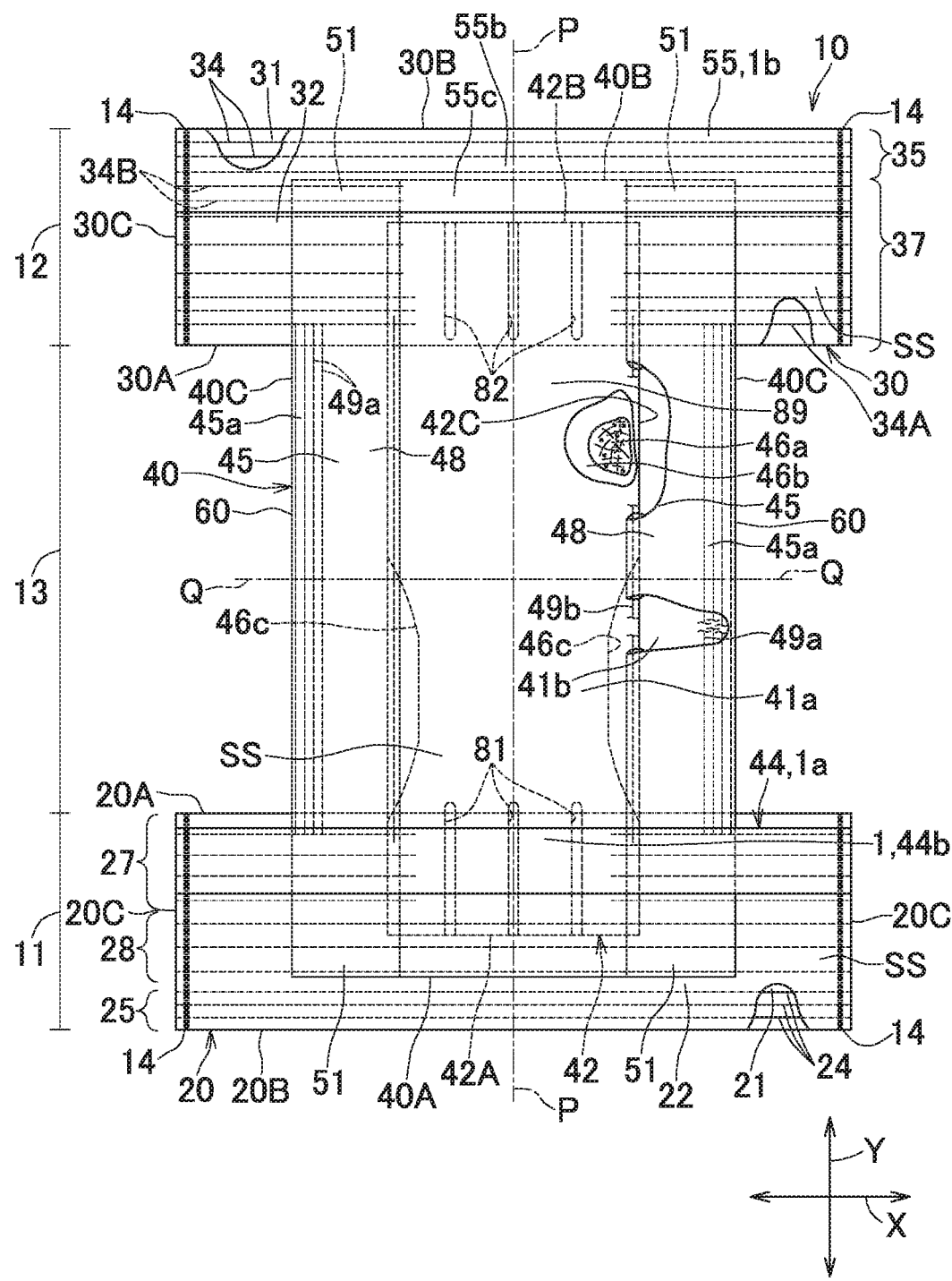
FIG. 2 is a partially cutaway plan view of the diaper 10 in a flatly opened sate obtained separating seams from the diaper in FIG. 1 and stretching each elastic member in a vertical direction and a lateral direction.
Figure 3:
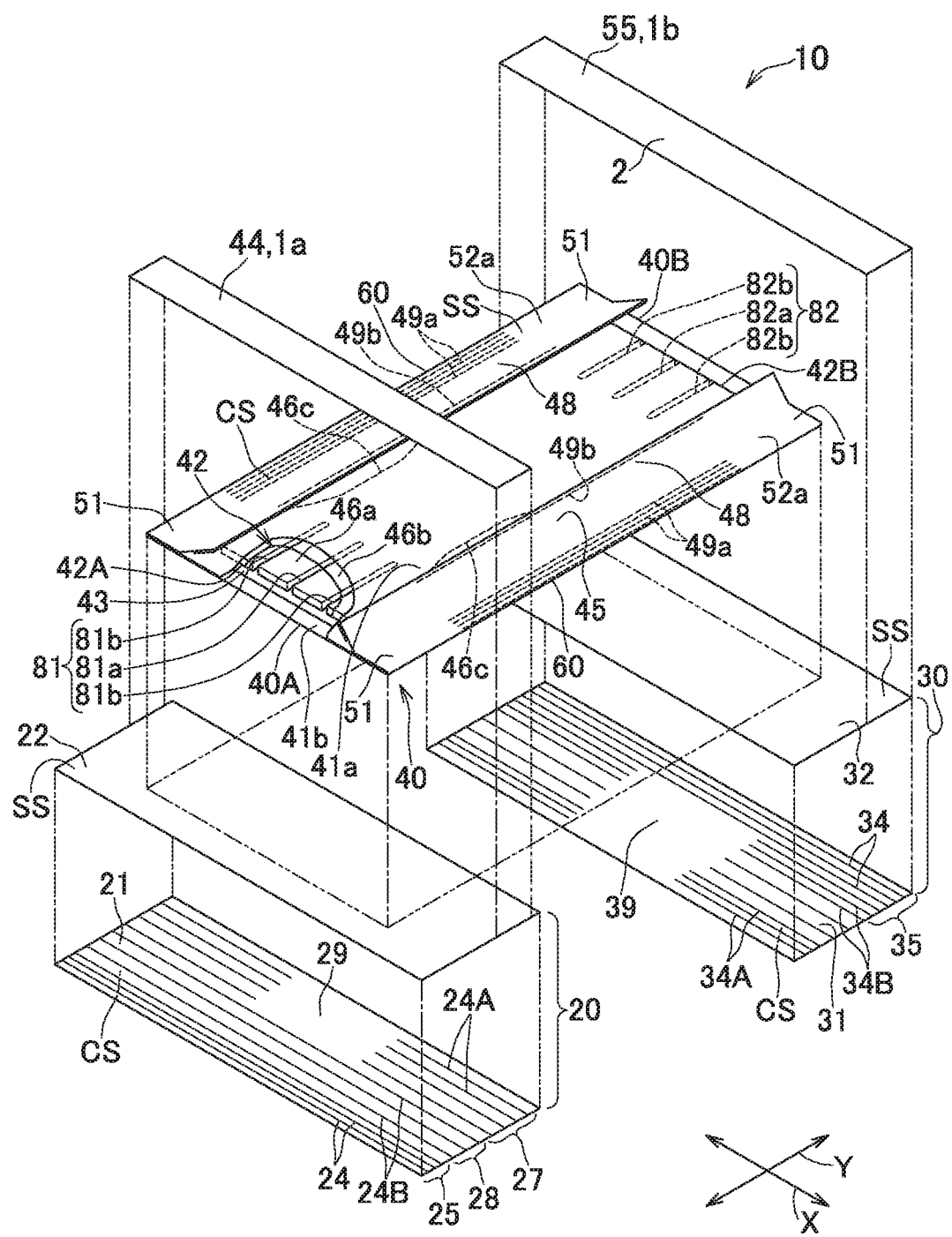
FIG. 3 is an exploded perspective view of the diaper in the flatly opened state.

FIG. 2 is a partially cutaway plan view of the diaper 10 in a flatly opened state with the front and rear waist panels 20 and 30 joined at the seams 14 being separated from each other and expanded to be to be in a planar state to the extent that gathers formed thereon disappears. FIG. 3 is an exploded view of the diaper 10 in FIG. 2. A double sided arrow Y in the figures indicates the vertical direction in FIG. 1.

The front and the rear waist panels 20 and 30 illustrated in FIGS. 2 and 3 have lower edges 20A and 30A extending in the lateral direction X, upper edges 20B and 30B opposed to the lower edges 20A and 30A extending in the lateral direction X, both side edges 20C extending in the vertical direction Y between the lower edge 20A and the upper edge 20B, and both side edges 30C extending in the vertical direction Y between the lower edge 30A and the upper edge 30B. The upper edges 20B and 30B are top edges of the front and the rear waist panels 20 and 30, respectively. Parts extending along both side edges 20C of the front waist panel 20 and both side edges 30C of the rear waist panel 30 are overlapped with each other as illustrated in FIG. 1, and coupled to each other in the seams 14 continually made in the vertical direction Y to define the waist opening 15. The crotch panel 40 extends between the lower edge 20A of the front waist panel 20 and the lower edge 30A of the rear waist panel 30.

The front waist panel 20 may include an outer sheet 21 and an inner sheet 22 respectively forming the clothing-facing surface CS and the skin-facing surface SS of the front waist region 11. A plurality of thread-like or strip-like front waist elastic members 24 are contractibly provided between the outer sheet 21 and the inner sheet 22 extending in the lateral direction X. Thus, a front waist elastic region 25 that is elastically contractible is defined in apart of the front waist panel 20 extending along the upper edge 20B. The front waist panel 20 is provided with an inner elastic strip 44 covering a part of the inner sheet 22 and extending across the crotch panel 40 toward both seams 14, preferably, to both seams 14. The inner elastic strip 44 has at least a middle part 44b (see FIG. 4) in the lateral direction X, functioning as an elastic band 1a in the front waist region 11. The elastic band 1a has a part in the crotch panel 40 positioned across at least an absorbent structure 42 (described later) without being joined to the crotch panel 40 and is elastically contractible in the lateral direction X.

The rear waist panel 30 may include an outer sheet 31 and an inner sheet 32 respectively forming the clothing-facing surface CS and the skin-facing surface SS in the rear waist region 12. A plurality of thread-like or strip-like rear waist elastic members 34 are contractibly provided between the outer sheet 31 and the inner sheet 32 extending in the lateral direction X. Thus, a rear waist elastic area 35 that is elastically contractible is formed in a part of the rear waist panel 30 extending along the upper edge 30B. The rear waist panel 30 is provided with an inner elastic strip 55 covering a part of the inner sheet 32 on the inner side of the diaper 10 and extending toward both seams 14, preferably, to both seams 14. The inner elastic strip 55 functions as an elastic band 1b in the rear waist region 12 of the diaper 10. The elastic band 1b is an example of an elastic band according to the present invention. The inner elastic strip 55 functioning as an elastic band 1b has at least a lower part 55c in a middle part 55b in the lateral direction X without being joined to a component part of the diaper facing the lower part 55c in a thickness direction of the inner elastic strip 55, and is elastically contractible in the lateral direction X.

The crotch panel 40 has a front edge 40A, a rear edge 40B, and both side edges 40C positioned between the front and the rear edges 40A and 40B. The crotch panel 40 may include the absorbent structure 42 having absorbability, which is provided between a top sheet 41a and a back sheet 41b. The top sheet may be formed of a liquid permeable sheet such as a liquid permeable fibrous nonwoven fabric defining the skin-facing surface SS. The back sheet 41b may be formed of a liquid-impermeable or hardly liquid permeable sheet (see FIG. 1 and FIGS. 5(a) and 5 (b)), defining the clothing-facing surface CS. A leakage-barrier sheet 43 formed of a plastic film is provided between the absorbent structure 42 and the back sheet 41b (see FIG. 5).

The absorbent structure 42 has a front edge 42A and a rear edge 42B extending in the lateral direction X and both side edges 42C extending between the front and the rear edges 42A and 42B. For example, the absorbent structure 42 may include a core material 46a formed of a mixture of fluff pulp and superabsorbent polymer particles and a liquid permeable wrapping sheet 46b formed of tissue paper or a nonwoven fabric covering the core material 46a. The core material 46a is curved to protrude from both side edges 46c toward outward on centering the vertical center line P.

The back sheet 41b of the crotch panel 40 has both side parts 45 extending in the lateral direction X from both side edges 42C of the absorbent structure 42. Both side parts 45 are each folded toward the vertical center line P along a corresponding one of fold lines 60, which are adjacent to both side edges of a leakage prevention sheet 43 and extend in the vertical direction Y, to have parts overlapping with each other. The overlapping parts are joined to each other with hot-melt adhesive HA2 (see FIG. 6) for example, in an end 51 in the upper and lower direction Y. The back sheet 41b has parts overlapping with each other joined to the front waist panel 20 and the rear waist panel 30 using hot-melt adhesive HA3 for example (see FIG. 6). Both side parts 45 further have leg surrounding flaps 45a and barrier cuffs 48 formed (see also FIG. 1). The leg surrounding flaps 45a each have a leg elastic member 49a extending in the vertical direction Y, and the barrier cuffs 48 each have a cuff elastic member 49b extending in the vertical direction Y.

Figure 4:
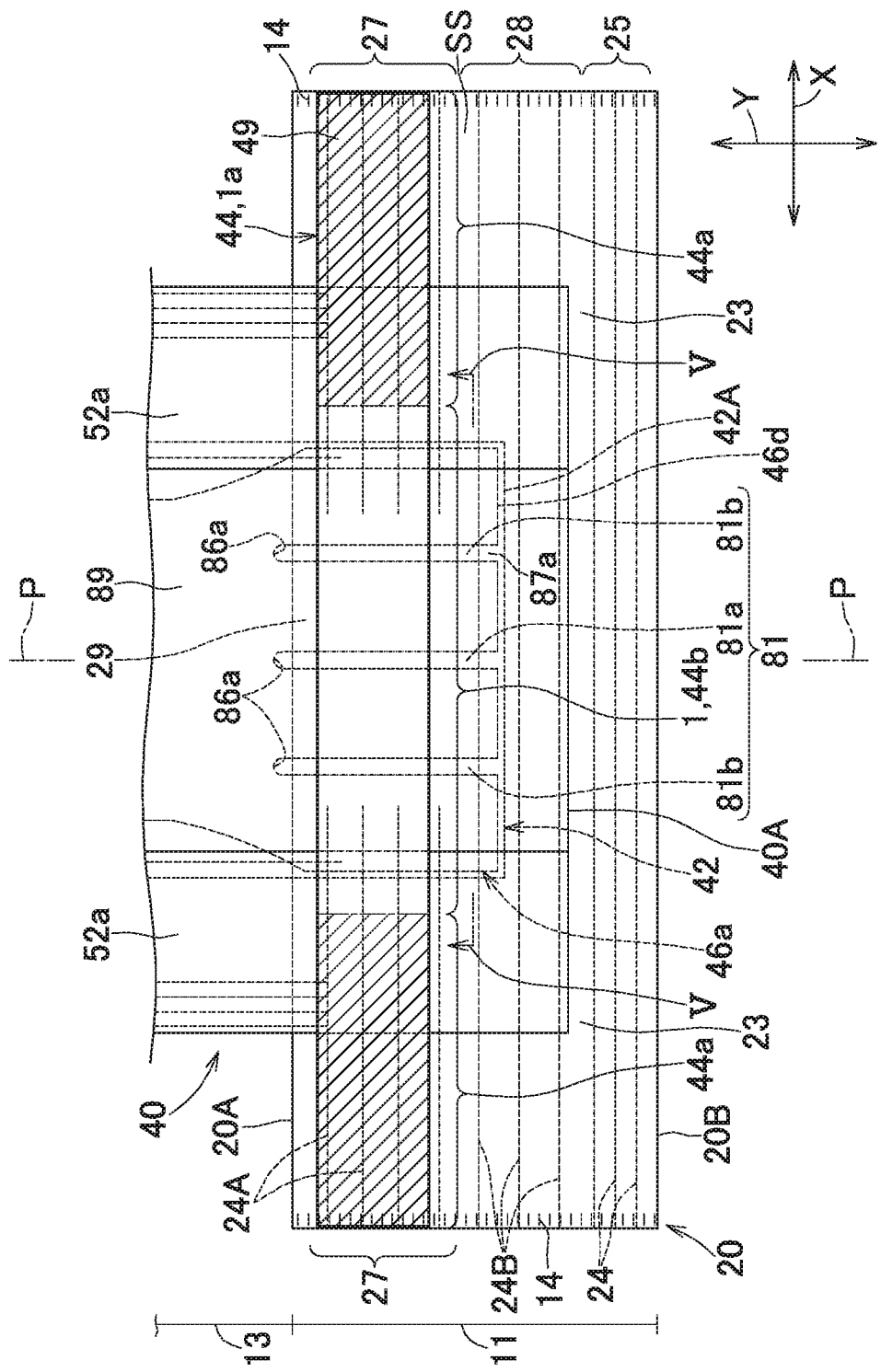
FIG. 4 is an enlarged view of a front waist panel in FIG. 2.

FIG. 4 is an enlarged view of the front waist panel 20 in FIG. 2 and a part of the crotch panel 40 overlapping with the front waist panel 20. In FIG. 4, the front waist panel 20 is provided with the plurality of front waist elastic members 24 extending in the lateral direction X, a plurality of first auxiliary elastic members 24A that are provided on the lower side of the front waist elastic member 24 and linearly extend along the lower edge 20A, and linearly extending second auxiliary elastic members 24B positioned between the front waist elastic members 24 and the first auxiliary elastic members 24A. The front waist elastic members 24, the first auxiliary elastic members 24A, and the second auxiliary elastic members 24B are in a string-like or strip-like form.

The front waist panel 20 has the plurality of front waist elastic members 24 provided more on the upper side than the front edge 40A of the crotch panel 40 and defining a front waist elastic area 25 extending in the lateral direction X along the upper edge 20B. The first auxiliary elastic members 24A do not extend across the core material 46a and are contractibly attached to both side parts of the front waist panel 20 and define a first auxiliary elastic areas 27 extending in the lateral direction X. The second auxiliary elastic members 24B contractibly extends between both seams 14 and defines a second auxiliary elastic area 28. The first auxiliary elastic areas 27 are a pair of elastic areas defined on both side parts in the lateral direction X with the absorbent structure 42 of the crotch panel 40 positioned therebetween, and is elastically contractible in the lateral direction X. A non-elastic area 29 that is not elastically contractible is defined between the pair of first auxiliary elastic areas 27 (see also FIG. 3). A second auxiliary elastic area 28 is positioned between the front waist elastic area 25 and the first auxiliary elastic area 27 and extends across the crotch panel 40. When the second auxiliary elastic members 24B are contracted, the second auxiliary elastic area 28 and the part of the crotch panel 40 overlapping with the second auxiliary elastic area 28 are contracted in the lateral direction X. The contraction of the front waist elastic area 25, the first auxiliary elastic area 27 and the second auxiliary elastic area 28 results in the multiple gathers 5 formed in the front waist panel 20 (see FIG. 1).

For example, spandex with 310 to 620 dtex may be stretched by a stretching ratio of 220 to 290% to be used as the front waist elastic member 24. Spandex with 310 to 620 dtex may be stretched by a stretch ratio of 270 to 370% to be used as the first auxiliary elastic members 24A. Spandex with 310 to 620 dtex may be stretched by a stretch ratio of 220 to 290% to be used as the second auxiliary elastic members 24B.

The inner elastic strip 44 illustrated in FIG. 4 has both side parts 44a in the lateral direction X joined to the inner sheet 22 of the front waist panel 20 and to both side partsportions 52a of the crotch panel 40 with hot-melt adhesive (not illustrated). Shaded areas 49 of the inner elastic strip 44 represent an example of the parts thus joined. The inner elastic strip 44 has at least the middle part 44b elastically stretched in the lateral direction, functioning as the elastic band 1a for forming the bulging part 100a (see FIG. 1 and FIG. 5 described later) in the front waist panel 20 and the crotch panel 40 upon being elastically contracted.

The middle part 44b of the inner elastic strip 44 in the state described above has an elastic contraction amount in the lateral direction X larger than that of a component part of the diaper (except for the inner elastic strip) facing the middle part 44b in the thickness direction of the inner elastic sheet 44 without being joined to the middle part 44b in the lateral direction X. In the illustrated example, this facing component part may include each part of the front waist panel 20 and the crotch panel 40. For example, the diaper 10 may be a diaper for infants. In such an example, a difference between the length of the middle part 44b in FIG. 4 in the lateral direction X and the length of the component part facing the middle part 44b in the lateral direction X is preferably in a range of 15 to 35 mm in the elastically contracted state, when the length of the middle part 44b in the lateral direction X is in a range of 50 to 100 mm. The bulging part 100a is formed by such a difference in the contraction amount and deformation guides 81 (described later).

The inner elastic strip 44 may be formed of a nonwoven fabric containing elastic yarns such as urethane elastic yarns to be capable of repeatedly elastically stretching and contracting, or a nonwoven fabric having an elastic member extending in the lateral direction X and attached thereto in the stretched state to be capable of repeatedly elastically stretching and contracting. The figure illustrates an example of the inner elastic sheet 44 containing the elastic yarns.

As further illustrated in FIG. 4, the core material 46a of the absorbent structure 42 has the deformation guides 81 extending from a front edge 46d toward the crotch region 13. The deformation guides 81 in the illustrated example are slits formed through the core material 46a and are positioned to overlap with the non-elastic area 29 of the front waist panel 20 in planary view of the diaper 10 in the stretched state. The deformation guides 81 in the illustrated example may include a center deformation guide 81a formed on and along the vertical center line P, and side deformation guides 81b and 81b positioned on both sides of the center deformation guide 81a in the lateral direction X.

The deformation guides 81 have upper ends 87a positioned at the front edge 46d of the core material 46a and lower ends 86a extending beyond the lower edge 20A of the front waist panel 20 without reaching a lateral center line Q (see FIG. 2) dividing equally the length of the diaper 10 in the stretched state in the upper and lower direction Y. In other words, the deformation guides 81 have the lower ends 86a positioned more on the upper side than the lateral center line Q, and an area 89 including no deformation guides 81 in the example illustrated in FIG. 4 is formed in a lowermost part of the crotch region 13 in FIG. 1.

The diaper 10 according to this embodiment may include the front waist panel 20 having the inner elastic strip 44 extending in the lateral direction X in the stretched state while covering a part of the skin-facing surface SS of the front waist panel 20. The inner elastic strip 44 has both side parts 44a in the lateral direction X, joined to both side parts 52a of the crotch panel 40 and to both side parts 23 of the front waist panel 20 on outer side parts of the side deformation guides 81b and 81b. The middle part 44b is positioned between both side parts 44a and is elastically contractible in the lateral direction X. The middle part 44b overlaps with the crotch panel 40 but is not joined to the crotch panel 40 at a part between the side deformation guides 81b and 81b to function as the elastic band 1a for forming the bulging part 100a in the front waist panel 20 and the crotch panel 40.

Figure 5A:
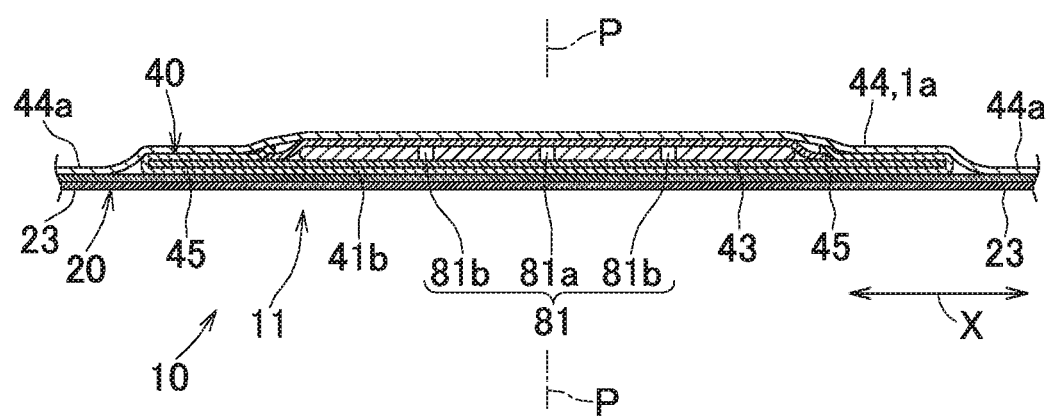
FIG. 5A is a cross-sectional view taken along line V-V in FIG. 4.
Figure 5B:
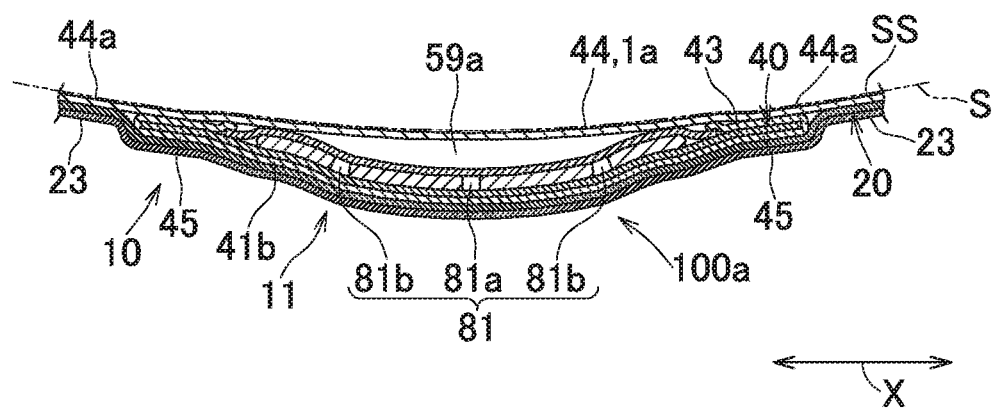
FIG. 5B is a schematic view illustrating a shape of a portion illustrated in FIG. 5A in the worn state.

FIG. 5A is a cross-sectional view taken along a line indicated by arrows V-V in FIG. 4, and FIG. 5B is a schematic view illustrating a state illustrated in FIG. 5A when the diaper 10 is in the worn state. This FIG. 5B may also be regarded as a cross-sectional view taken along a line indicated by arrows b-b in FIG. 1A. In FIG. 5A, the crotch panel 40 overlapping with the front waist panel 20 has an upper part provided with the deformation guides 81. Thus, when the inner elastic strip 44 functioning the elastic band 1a contracts in the lateral direction X, the part of the front waist panel 20 overlapping with the deformation guides 81 and the part between the side deformation guides 81b and 81b are convexly curved outward from the diaper 10, whereby the bulging part 100a in a round shape is formed. Thus, a wearer in a standing posture may change to a sitting posture to have the abdominal region protruding forward without being oppressed due to the bulging part 100a formed in the diaper 10.

In the bulging part 100a, the front waist panel 20 and the crotch panel 40 overlapping thereon deform in a protruding manner to be spaced apart from the wearer's body with the inner elastic strip 44 being in close contact with the skin S, whereby a space 59a that may allow body exudates to flow thereinto is formed between the skin S and the crotch panel 40 (see FIG. 5B).

As exemplarily illustrated in FIG. 5B, the bulging part 100a is formed in the part of the crotch panel 40 where the deformation guides 81 are provided. The contraction amount of the inner elastic strip 44 is substantially consistent among wearers. Thus, a consistent position and size of the bulging part 100a as well as a consistent outer view of the diaper 10 may be achieved in the worn state. Both side parts 23 of the front waist panel 20 adjacent to the bulging part 100a (see also FIG. 4) and both side parts 45 of the crotch panel 40 are integrated with both side parts 44a of the inner elastic strip 44 to be in close contact with the skin S of the wearer (see FIG. 5). Thus, the diaper 10 does not have an outer view giving a bulky impression as a whole, and may prevent body exudates contained in the space 59a from spreading in the lateral direction X.

Figure 6:
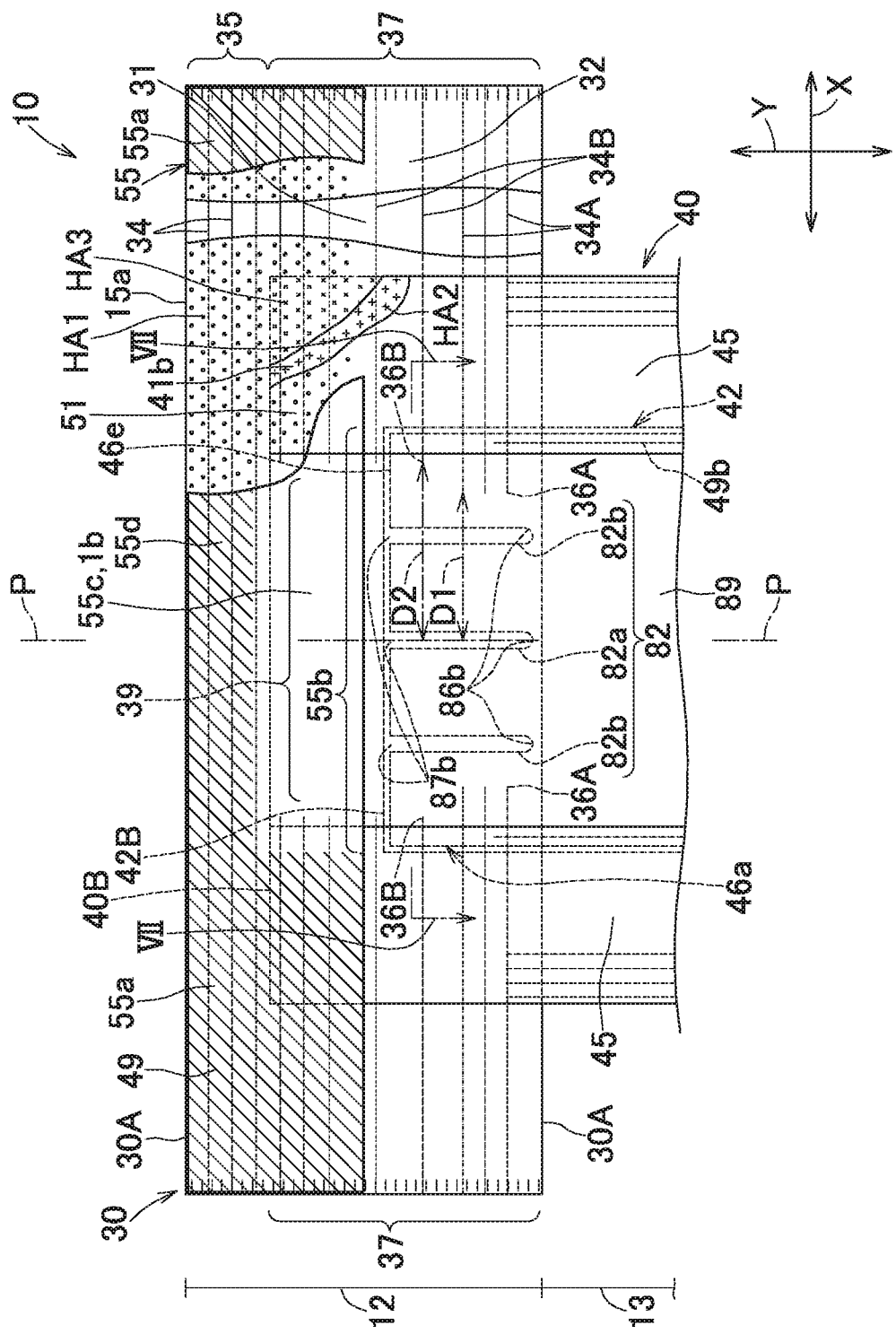
FIG. 6 is a partially cutaway enlarged view of a rear waist panel in FIG. 2.

FIG. 6 is an enlarged view of a part of the crotch panel 40 and the rear waist panel 30 in FIG. 2. The rear waist panel 30 illustrated in FIG. 6 has the rear waist elastic members 34 provided between a peripheral edge 15a of the waist opening 15 and the rear edge 40B of the crotch panel 40, and defines the rear waist elastic area 35 extending in the lateral direction X along the peripheral edge 15a. The rear waist panel 30 has a plurality of first auxiliary elastic members 34A and a plurality of second auxiliary elastic members 34B provided on the lower side of the rear waist elastic members 34 in the stretched state. The first and the second auxiliary elastic members 34A and 34B form a pair of auxiliary elastic areas 37 provided on both side parts of the rear waist panel 30 without extending across the absorbent structure 42 to face each other in the lateral direction X with the absorbent members 42 provided in between. A non-elastic area 39 including no elastic member in the stretched state (see also FIG. 3) is formed between the auxiliary elastic areas 37. The first and the second auxiliary elastic members 34A and 34B respectively have inner ends 36A and 36B facing the vertical center line P. A length D1 between the vertical center line P and the inner end 36A is shorter than a length D2 between the vertical center line P and the inner end 36B. Thus, a distance between the inner ends 36A facing each other in the lateral direction X, that is, a length obtained by doubling D1 is smaller than a distance between the inner ends 36B, that is, a length obtained by doubling D2.

The inner elastic strip 55 in the rear waist panel 30 is formed of a nonwoven fabric containing elastic yarns such as urethane elastic yarns capable of elastically stretching and contracting or a nonwoven fabric having an elastic member extending in the lateral direction X attached thereto in the stretched state capable of elastically extending. The inner elastic strip 55 has a part overlapped with the rear waist elastic area 35 and has both side parts 55a, in the lateral direction X, joined to the inner sheet 32 and both side parts 45 of the crotch panel 40 with hot-melt adhesive HA1 for example. In FIG. 6, the shaded area 49 represent the parts of the inner elastic strip 55 joined to the inner sheet 32 and the crotch panel 40 for easy understanding. The inner elastic strip 55 may include the middle part 55b positioned between the both side parts 55a and 55a in the lateral direction X. The middle part 55b has the lower part 55c not joined to the rear waist panel 30 and the crotch panel 40 overlapping with the lower part 55c, and has an upper part 55d positioned immediately above the lower part 55c, joined to the rear waist panel 30 with the hot-melt adhesive HA1 for example. The lower part 55c is a part of the middle part 55b spreading below the rear waist elastic area 35.

The middle part 55b illustrated in FIG. 6 has the elastic contraction amount of the lower part 55c in the lateral direction X set to be larger than that of a part of rear waist panel 30 facing the lower part 55c in the thickness direction of the inner elastic strip 55 without being joined to the lower part 55c. In an example where the diaper 10 is for infants, the difference between the length of the lower part 55c in the lateral direction X and the length of the part of the rear waist panel 30 facing the lower part 55c in the lateral direction X is preferably in a range of 15 to 35 mm in the elastically contracted state, when the length of the middle part 55b in the lateral direction X is in a range of 50 to 100 mm.

The absorbent structure 42 illustrated in FIG. 6 has deformation guides 82 formed in the core material 46a. The deformation guides 82 in the illustrated example overlaps with the non-elastic area 39 of the rear waist panel 30 and may or may not overlap with the inner elastic strip 55 in planary view of the diaper 10 in the stretched state. The figure illustrates the non-overlapping state. The deformation guides 82, which are slits formed in the core material 46a, extends toward the lower side from a rear edge 46e of the core material 46a, and the lower ends 86b may or may not extend beyond the lower edge 30A of the rear waist panel 30. The figure illustrates the state where the lower end 86b does not extend beyond the lower edge 30A. The lower end part 86b does not reach the lateral center line Q (see FIG. 2). The crotch region 13 has the area 89 without the deformation guides 82 formed between the lateral centerline Q and the lower end 86b. The deformation guides 82 in the illustrated example may include a center deformation guide 82a positioned on the vertical center line P and a pair of side deformation guides 82b and 82b that are on both sides of the center deformation guide 82a in the lateral direction X, and are symmetrical relative to the vertical center line P.

Figure 7A:
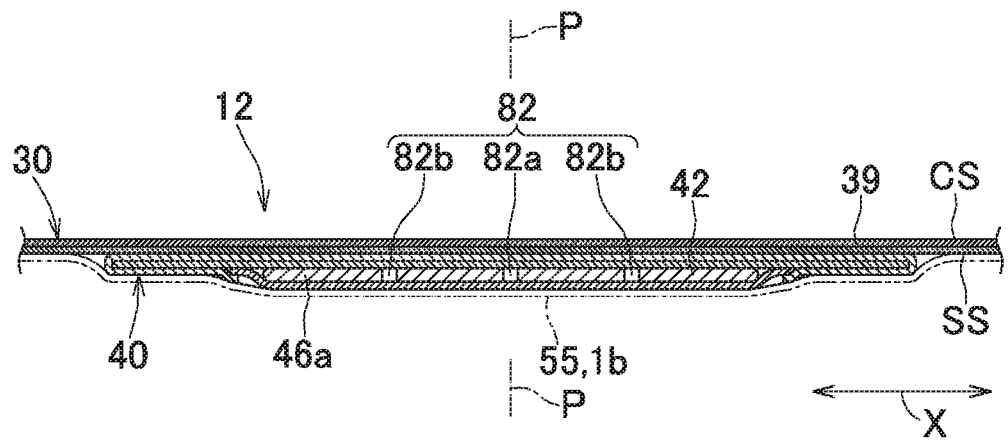
FIG. 7A is a cross-sectional view taken along line VII-VII in FIG. 6.
Figure 7B:
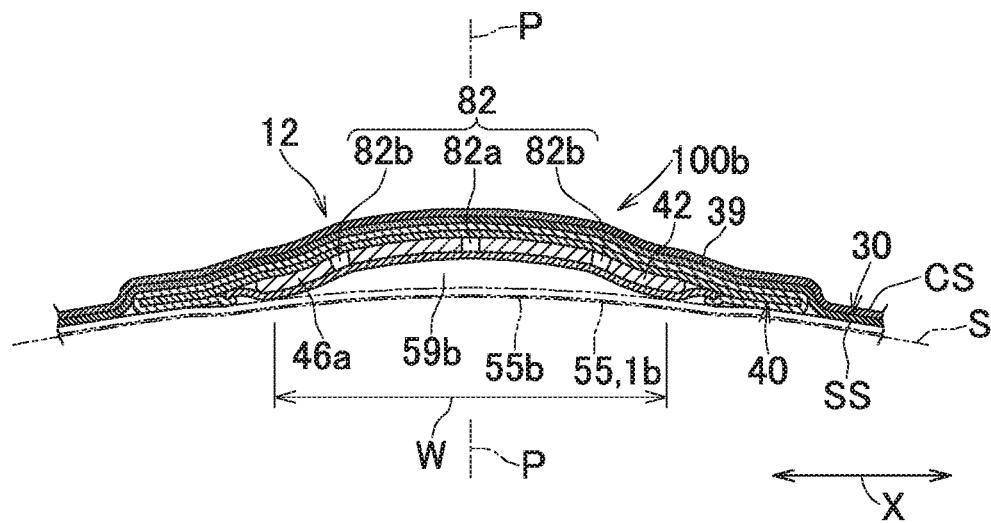
FIG. 7B is a schematic view illustrating a shape of a part illustrated in FIG. 7A in the worn state.

FIG. 7A is a cross-sectional view taken along a line indicated by arrows VII-VII in FIG. 6 and FIG. 7B is a schematic view illustrating a state illustrated in FIG. 7A, when the diaper 10 is in the worn state. In FIGS. 7(a) and 7(b), the inner elastic strip 55 is illustrated with a dotted line. The line indicated by the arrows VII-VII extends across the non-elastic area 39 of the rear waist panel 30. When the lower part 55c (see FIG. 6) of the inner elastic strip 55 contracts in the lateral direction X in the state illustrated in FIG. 7A, the non-elastic area 39 of the rear waist panel 30, which is in a flat state and does not elastically contract, and the part of the crotch panel 40 overlapping with the non-elastic area 39 are curved to protrude toward the clothing-facing surface CS from the skin-facing surface SS by the deformation guides 82 in the crotch panel 40. Thus, the bulging part 100b (see also FIG. 1B) in a round shape is formed, and a space 59b is formed between the skin S of the wearer and the bulging part 100b. The rear waist panel 30 and the crotch panel 40 are each in contact with the skin S on both outer side parts of the space 59b in the lateral direction X under the contraction of the rear waist elastic members 34, the first auxiliary elastic members 34A, and the second auxiliary elastic members 34B in the rear waist panel 30 (see FIG. 6). The core material 46a in the crotch panel 40 is sectionalized in the lateral direction X with the deformation guides 82, and thus may easily deform. Thus, a part more on the outer side than the side deformation guides 82b may easily fit a shape of the buttocks.

In the diaper 10 in the worn state, body exudates such as loose stool flowing from the crotch region 13 toward the rear waist region 12 may be contained in the space 59b. As described above, the inner elastic strip 55, the lower part 55c of the inner elastic strip 55 in particular, functions as the elastic band 1b for forming the bulging part 100b in the rear waist panel 30 and the crotch panel 40.

A length W of the space 59b in a part where the rear waist panel 30 and the crotch panel 40 overlap with each other in the lateral direction X may be affected by a length (the length that is double the length D1 in FIG. 6) between the first auxiliary elastic members 34A in the lateral direction X and by a length (the length that is double the length D2 in FIG. 6) between the second auxiliary elastic members 34B. The bulging part 100b may be formed with the crotch panel 40 having a part between the side deformation guides 82b and the first auxiliary elastic members 34A and a part between the side deformation guides 82b and the second auxiliary elastic members 34B curving as well, instead of sharply curving at the side deformation guides 82b and 82b. In the example illustrated in FIG. 6, the lengths satisfy relationship D1<D2. Thus, the length W of the space 59b in a width direction in FIG. 7B is likely to decrease in a part where the first auxiliary elastic members 34A face each other in the lateral direction X and increase in a part where the second auxiliary elastic members 34B face each other in the lateral direction X, from the lower edge 30A toward the upper edge 30B of the rear waist panel 30. Loose stool flowed in the space 59b in the configuration described above is less likely to flow out from the space 59b, and thus stays in the space 59b. The bulging part 100a defining the space 59b has a round shape with the length W gradually increasing from the lower side toward the upper side.

For example, spandex with 310 to 620 dtex may be stretched by a stretch ratio of 220 to 290% to be used as the rear waist elastic members 34. Spandex with 310 to 620 dtex may be stretched by a stretch ratio of 280 to 380% to be used as the first and the second auxiliary elastic members 34A and 34B.

The deformation guides according to the present invention including the deformation guides 81 and 82 for example may include the deformation guides 81 only or the deformation guides 82 only. The quantity, the length in the vertical direction Y, and the length in the lateral direction X of the deformation guides to be formed may be freely set as long as the operations and effects as described above may be achieved. For example, the deformation guides 81 and 82 may each have the length in the vertical direction Y set to be 15 to 60 mm, and have the length in the lateral direction X set to be 2 to 10 mm. The deformation guides 81a and 81b and/or the deformation guides 82a and 82b may have the same lengths and shape as in the illustrated example, or may have different lengths and shapes.

The deformation guides 81 and 82 according to the present embodiment are slits extending toward the lower side from the front edge 46d and the rear edge 46e of the core material 46a, but may also be through holes formed on the lower side of the front edge 46d and/or the rear edge 46e. The deformation guides may be a bottomed groove formed by partially compressing the core material 46a. The groove thus formed in the core material 46a preferably has a depth direction extending from the skin-facing surface SS toward the clothing-facing surface CS. The deformation guides may be formed by setting the density of the core material 46a formed of superabsorbent polymer particles, fluff pulp or the like to be higher or lower than the density in apart other than the deformation guides. These deformation guides may be formed to include or not include the wrapping sheet 46b. The deformation guides 81 according to the present embodiment extends beyond the lower edge 20A of the front waist panel 20, but may not extend beyond the lower edge 20A.

The length D1 and the length D2 according to the present embodiment may be the same value. Still, when the length D1 is set to be smaller than the length D2 as described above, the space 59b formed in the rear waist region 12 may be designed to be larger on the inner side than on the opening side so that the accommodated body exudates may be prevented from flowing back toward the opening side of the space 59b.

The deformation guides 81 and the inner elastic strip 44 provided in the front waist panel 20 in the illustrated example may be used for the rear waist panel 30 instead of the deformation guides 82 and the inner elastic strip 55 in the rear waist panel 30. Similarly, the deformation guides 82 and the inner elastic strip 55 may be used for the front waist panel 20.

The positional relationship between the deformation guides 81 and the inner elastic strip 44 is not limited to the illustrated example. For example, the deformation guides 81 and the inner elastic sheet 44, in FIGS. 2 and 4, may not overlap with each other. The inner elastic strip 44 in the front waist panel 20 may be positioned to be more on the upper or lower side than the position illustrated in the figure. The inner elastic strip 55 in the rear waist panel 30 illustrated in FIG. 6 may extend toward the lower side to be overlapped with the absorbent structure 42.

The disposable absorbent wearing article according to present invention has the configuration as described above so as to be suitably used as disposable diapers not only for infants but also for incontinent male patients or the like. In such an instance, the space 59a illustrated in FIG. 5B serves as a space suitable for containing the penis or a urine absorbent pad.

Figure 8:
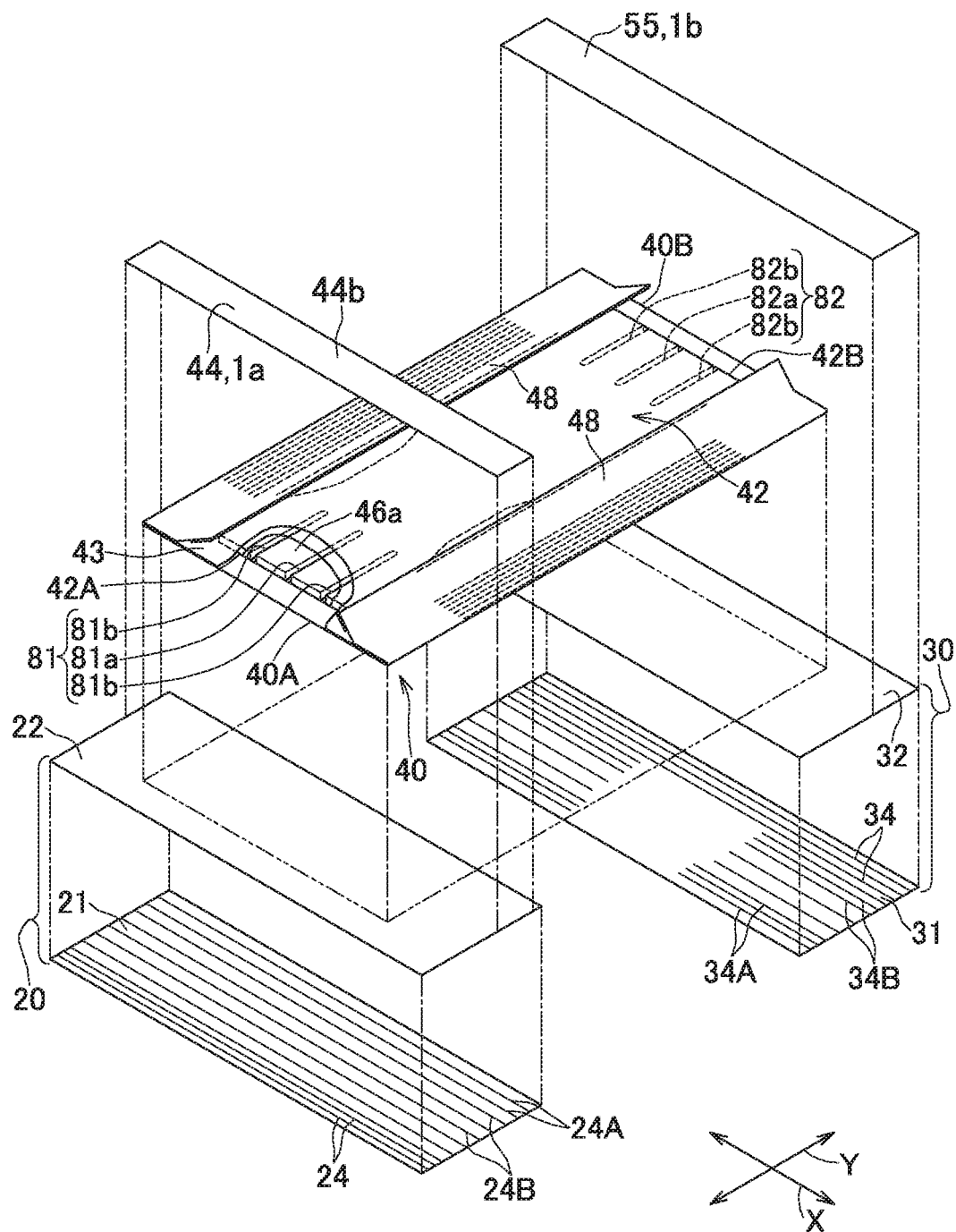
FIG. 8 is a diagram similar to FIG. 3 illustrating one exemplary embodiment.

FIG. 8 is a diagram, similar to FIG. 3, illustrating one exemplary embodiment. The front waist panel 20 illustrated in FIG. 8 has the first auxiliary elastic members 24A in the example illustrated in FIG. 3, extending in the lateral direction X to extend across the core material 46a. The first auxiliary elastic members 24A may be in an elastically stretched and contracted state or in a state of not being capable of contracting due to the loss of elasticity in a part provided over the core material 46a. In any instances, the front waist panel 20 is designed to have the elastic contraction amount in the lateral direction X in the part facing the center part 44b of the inner elastic strip 44 set to be smaller than the elastic contraction amount of the middle part 44b of the inner elastic strip 44 in the lateral direction X. In this embodiment, the first auxiliary elastic members 24A and the second auxiliary elastic members 24B needs not to be distinguished from each other, and thus may be simply and collectively referred to auxiliary elastic members.

Figure 9:
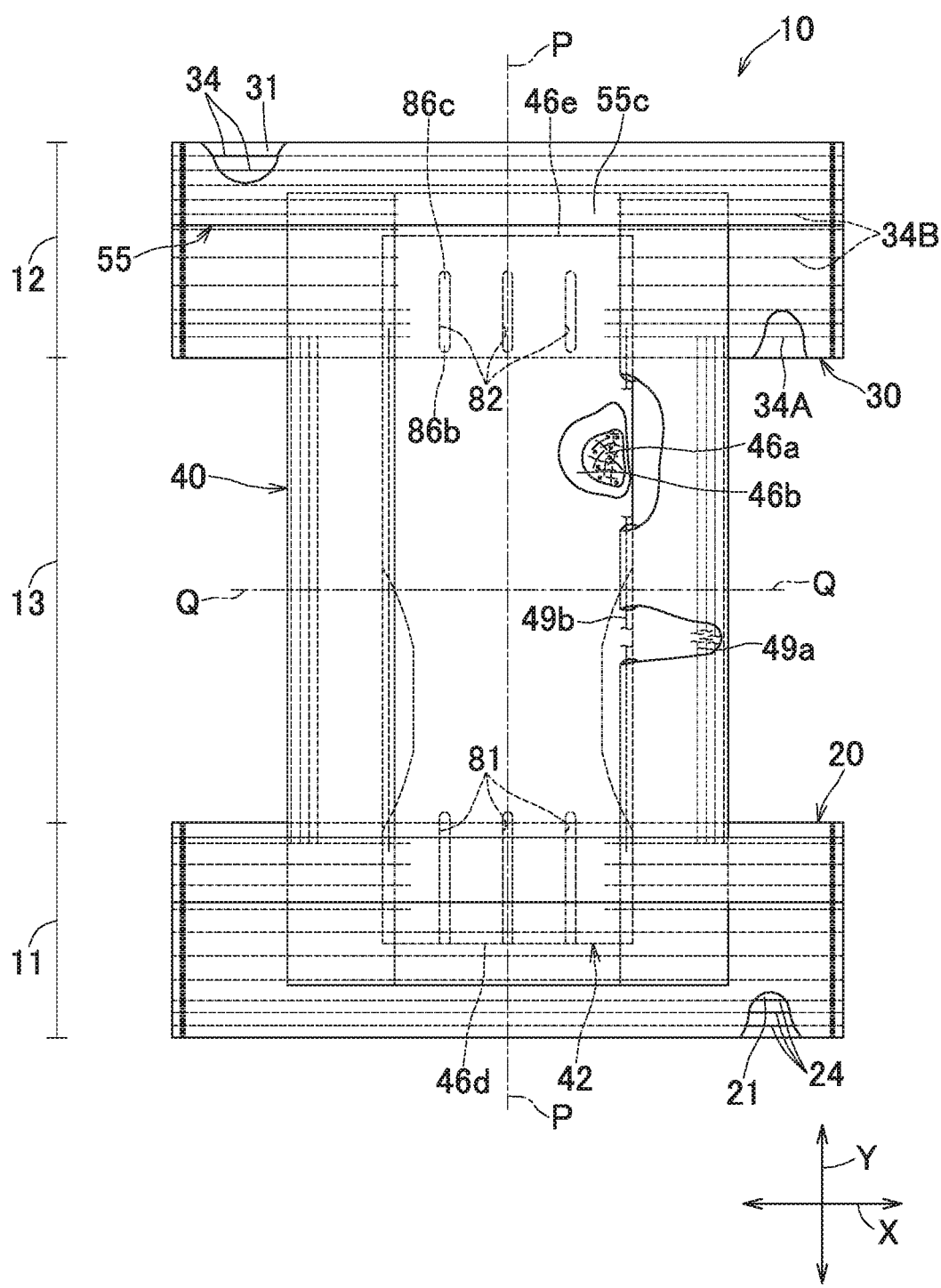
FIG. 9 is a diagram similar to FIG. 2 illustrating another exemplary embodiment.

FIG. 9 is a diagram similar to FIG. 2 illustrating another exemplary embodiment. A diaper with an outer view similar to that of the diaper 10 in FIG. 1 may be obtained from the diaper 10 in the stretched state in FIG. 9. The core material 46a of the diaper 10 in the stretched state has the deformation guides 81 with the shape and the position that are the same as those in FIGS. 2 and 4, but has the deformation guides 82, which are slits, with the shape and the position that are different from those in FIGS. 2 and 6.

The deformation guides 82 in FIG. 9 has both upper and lower ends 86b and 86c in the vertical direction Y positioned between the rear edge 46e and the lateral center line Q and not crossing the rear edge 46e of the core material 46a. When the lower part 55c of the inner elastic sheet 55 in the rear waist panel 30 is contracted, the absorbent structure 42 deforms to be convexly curved in a round shape, and the deformation guides 82 each deform to have a width increasing in the lateral direction X. Thus, the rear waist panel 30 and the crotch panel 40 form a bulging part similar to the bulging part 100b in the example illustrated in FIG. 7B in a round shape in the lateral direction X, and a space similar to the space 59b (see FIG. 7) is formed on the inner side of the bulging part. Although not elaborated in the figure, in the present invention, the deformation guides. 81 of the core material 46a may be positioned between the front edge 46d and the lateral center line Q without crossing the front edge 46d of the core material 46a.

Figure 10A:
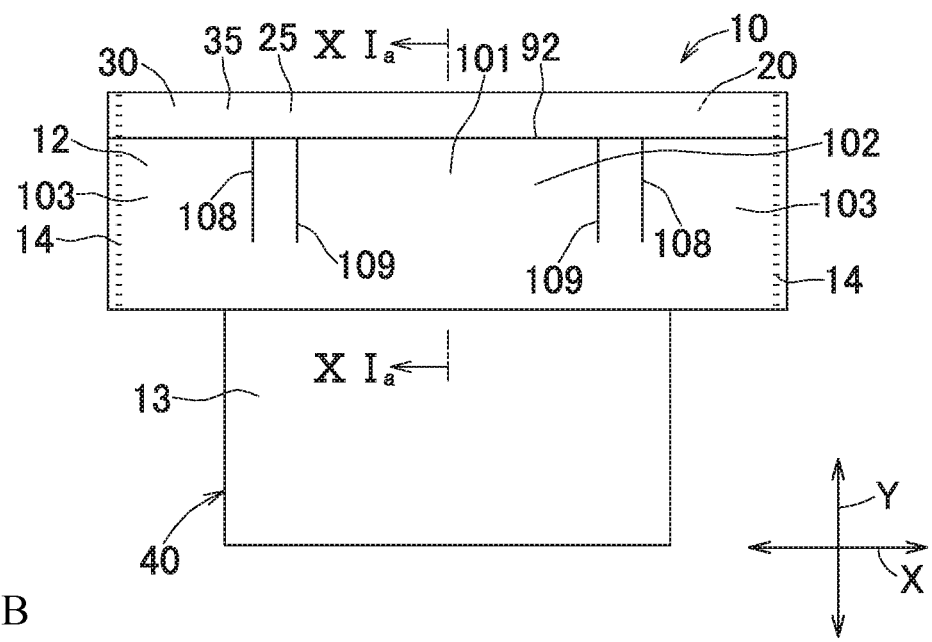
FIG. 10A is a rear view of a disposable diaper according to another exemplary embodiment.
Figure 10B:
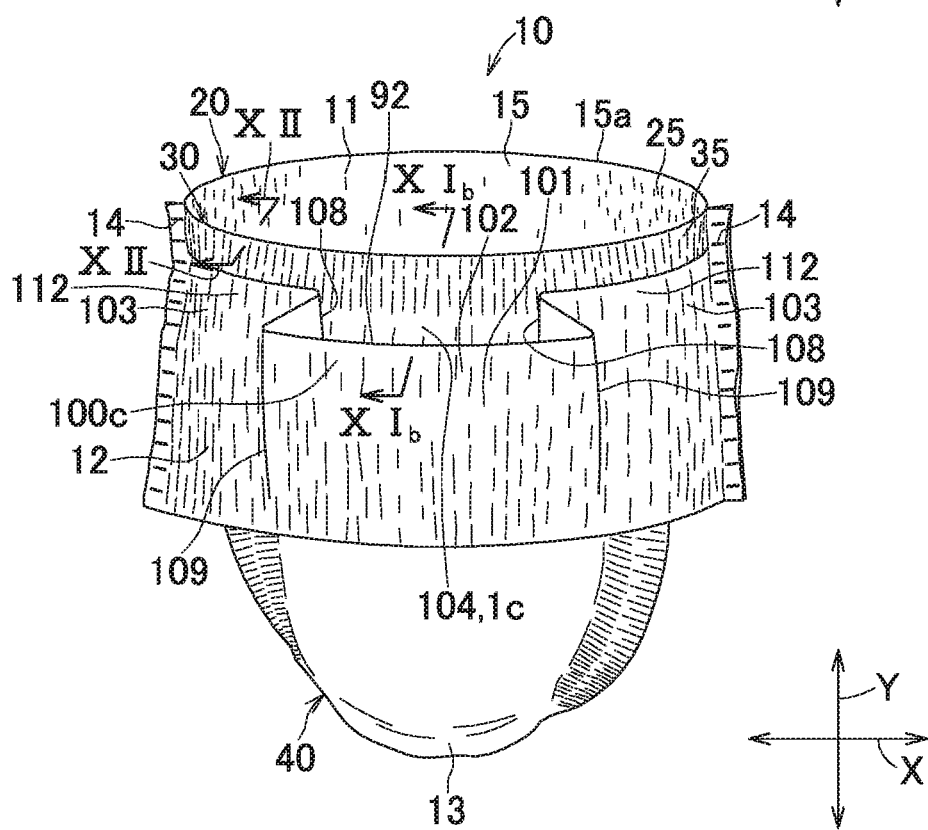
FIG. 10B is a rear view of the diaper in the worn state.

FIG. 10A is a back view of a disposable diaper 10 according to one exemplary embodiment. Elastic members (see FIGS. 11 and 12) such as a later-described rear waist elastic member 34 used in the diaper 10 is in a state of being stretched in the lateral direction X or in the vertical direction Y. FIG. 10B is a back view of the diaper 10 in the worn state in FIG. 10A.

In FIG. 10A, the diaper 10 may include the front waist panel 20, the rear waist panel 30, and the crotch panel 40. The rear waist panel 30 has a fold part 92 (see also FIGS. 11(a) and 11(b)) extending in the lateral direction X. A pair of joining lines 108 and a pair of folding guide lines 109 extending toward the lower side from the fold part 92. As is clearly illustrated in FIG. 11, an inner part 104, an outer part 105, and an intermediate part 106 in a middle part 101 between the joining lines 108 and 108 overlap with each other without being joined to each other. As is clearly illustrated in FIG. 12 described later, the inner part 104, the outer part 105 and the intermediate part 106 are joined to each other in a side 103 between the joining line 108 and the seam 14.

The diaper 10 further has a folded part 102 formed in the middle part 101. The diaper 10 illustrated in FIG. 11B has the folded part 102 expanding outward from the diaper 10 so that a bulging part 100c is formed. The bulging part 100c is likely to be a substantially consistent shape, as in the illustrated example due to folding guide lines 109 formed in the rear waist panel 30. The bending guide lines 109 are not necessarily required in the rear waist panel 30 but are provided to facilitate the formation of the bulging part 100c in particular. These parts may be obtained by creasing the rear waist panel 30 in advance, in a process of manufacturing the rear waist panel 30 for example.

The diaper 10 further has the side 103 in the rear waist panel 30 coming into contact with the skin S of the wearer (see FIG. 11B and FIG. 12) under a contracting action of the first and the second auxiliary elastic members 34A and 34B in the side portions 103. The front waist panel 20 in FIG. 10B is the same as the front waist panel 20 illustrated in FIGS. 2 to 4. The rear waist panel 30 is as described later. The front waist panel 20 and the rear waist panel 30 further have the front and rear waist elastic areas 25 and 35 coming into contact with the skin S of the wearer. The front and rear waist elastic areas 25 and 35 extend along the top edges of the front and the rear waist panels 20 and 30 serving as the peripheral edge 15a of the waist opening 15.

Figure 11A:
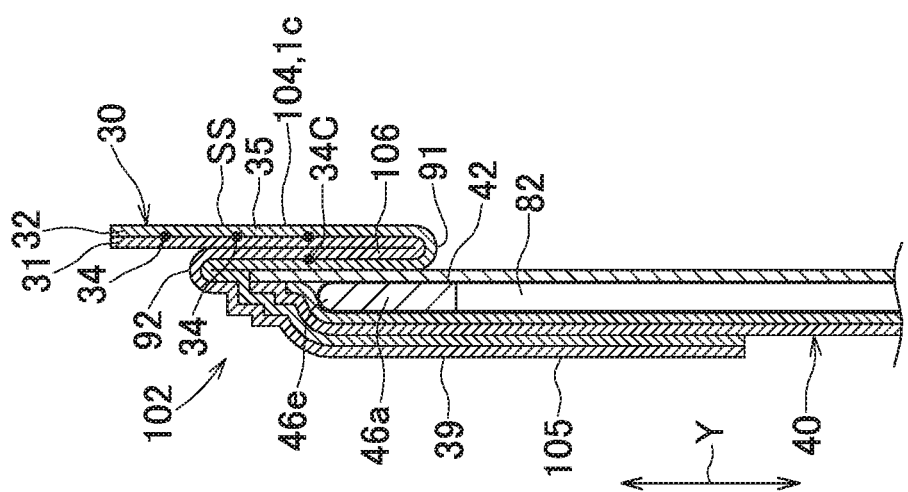
FIG. 11A is a cross-sectional view taken along line $XI_a$-$XI_a$ in FIG. 10A.
Figure 11B:
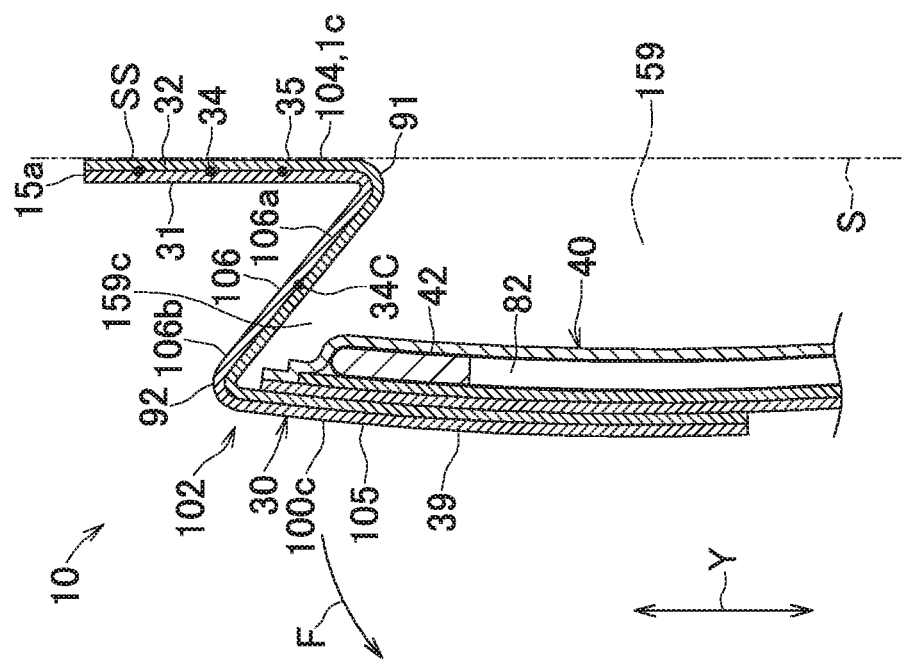
FIG. 11B is a cross-sectional view taken along line $XI_b$-$XI_b$ in FIG. 10B.

FIGS. 11(a) and 11(b) are partial cross-sectional views taken along lines XI$_a$-XI$_a$ and XI$_b$-XI$_b$ in FIGS. 10(a) and 10(b) respectively. FIG. 11A illustrates the rear waist panel 30 including the outer sheet 31 and the inner sheet 32 joined to each other with hot-melt adhesives (not illustrated) as the rear waist panel 30 illustrated in FIG. 2, and further may include the rear waist elastic member 34 that is provided between the outer sheet 31 and the inner sheet 32 and is joined to at least one of the outer sheet 31 and the inner sheet 32 while being in a stretched state. The crotch panel 40 is joined to the skin-facing surface SS of the inner sheet 32 with hot-melt adhesive (not illustrated). The core material 46a in the absorbent member 42 of the crotch panel 40 has slits serving as the deformation guides 82 as in the crotch panel 40 in the example illustrated in FIG. 9. The figure illustrates a plurality of slits extending in the vertical direction Y on the lower side of the rear edge 46e of the core material 46a. Also in this configuration, the slits serve as the deformation guides that facilitates the rearward bulging of the crotch panel 40 in the front and rear direction of the diaper 10 and folding of the rear waist panel 30 and the crotch panel 40 in the lateral direction X. The deformation guides 82 in the illustrated example is an example of a part not overlapping with the inner part 104 of an elastic band 1c (described later) in the thickness direction of the core material 46a.

In FIGS. 11(a) and 11(b), the rear waist panel 30 is folded at the fold parts 91 and 92 formed in parts more on the lower side than the rear waist elastic area 35 to have parts overlapping with each other, whereby the folded part 102 is formed that is folded into a Z shape together with the rear waist elastic area 35. Specifically, the folded part 102 is formed by a part of the rear waist elastic area 35 may include the inner part 104 that is elastically contractible in the lateral direction X, and further may include the outer portion 105 and the intermediate part 106 formed of the non-elastic area 39 (see FIG. 3) that is an area in the rear waist panel 30, including no elastic member. As in the illustrated example, the auxiliary elastic member 34C may be used in the intermediate part 106. The auxiliary elastic member 34C has spandex of 310 to 620 dtex stretched by a stretch ratio of 140 to 180%, so that the intermediate part 106 in the state illustrated in FIG. 11B may be prevented from further leaning outward of the diaper 10. The outer portion 105 is not elastically contractible in the lateral direction X. The intermediate part 106 is not elastically stretchable in the lateral direction X.

Figure 12:
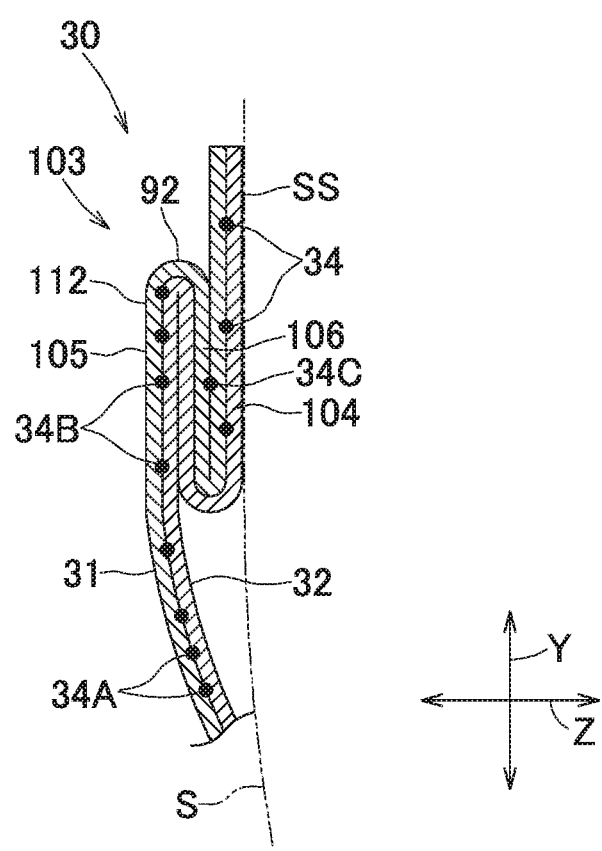
FIG. 12 is a cross-sectional view taken along line XII-XII in FIG. 10B.

FIG. 12 is a cross-sectional view of the rear waist panel 30 taken along line XII-XII in FIG. 10B. The line XII-XII is a cutting line passing through the side parts 103 of the rear waist panel 30. The side part 103 in FIG. 12 has a folded part 112 having a cross-sectional shape, along the upper and lower direction Y in a shape of the letter Z. In the folded part 112, the inner part 104, the outer part 105 and the intermediate part 106 overlap with each other and are joined to each other with hot-melt adhesive (not illustrated), and continues to the inner part 104, the outer part 105 and the intermediate part 106 in FIG. 11. In the outer part 105 in FIG. 12, the first and the second auxiliary elastic members 34A and 34B extending in the lateral direction X in the stretched state are provided between the outer sheet 31 and the inner sheet 32.

In the rear waist panel 30 of the diaper 10 in the state illustrated in FIGS. 10 to 12, when the inner part 104 of the center part 101 is elastically contracted in a circumference direction or the wearer's waist, the intermediate part 106 facing the inner part 104 without being joined to the inner part 104 in the thickness direction of the inner part 104 has a part 106a connected to the inner part 104, contracted to follow the contacting the movement of the inner part 104. The intermediate part 106 further has a part 106b that is connected to the outer part 105 and is difficult to follow the movement of the inner part 104. Thus, the length of the intermediate part 106 in the lateral direction X does not substantially change even when the length of the intermediate part 106 in the lateral direction X is reduced by the same level as the length of the inner part 104. The outer part 105 facing the inner part 104 with the intermediate part 106 provided in between is connected to the rear waist elastic region 35 via the fold parts 91 and 92, and is joined to the crotch panel 40 with high bending stiffness. Thus, the length of the outer part 105 in the lateral direction X almost does not change or does not change at all, when the inner portion 104 is contracted.

Thus, the contraction amount as a result of the elastic contraction of the inner part 104 is larger than the contraction amount as a result of the contraction of at least the outer portion 105 in the outer part 105 and the intermediate part 106. The contraction amounts are compared with each other as described later. When the inner part 104 with a large contraction amount is contractible in the lateral direction X, the outer part 105 and the part 106b of the intermediate part 106 with a small elastic contraction amount form the bulging part 100c illustrated in FIG. 10B that is protruded outward in a radial direction of the waist opening 15 and curved in the lateral direction X. Thus, a space 159 from the skin S of the diaper wearer is formed as illustrated in FIG. 11B. The diaper 10 illustrated in FIG. 11B has the bulging part 100c further expanding in a direction indicated by an arrow F when the contraction amount of the inner part 104 increases from that in the illustrated example. The space 159 may contain body exudates from a wearer, as in the space 59*b* in FIG. 7. In FIG. 11B, the outer part 105 and the intermediate part 106 with a downward opening. The pocket 159*c* is a part of the space 159. The inner part 104 with the configuration described above functions as the elastic band 1*c* of the diaper 10 in FIG. 10A.

The diaper 10 in the example illustrated in FIGS. 10 to 12 also has the side parts 103 positioned on both sides of the space 159 formed in the middle part in the lateral direction X, coming into contact with the skin S of a wearer when elastic contracting force is applied (see FIG. 10B and FIG. 12). Thus, the diaper 10 may have a consistent expanding part of the rear waist panel 30 for forming the space 159 on the inner side of the part, even when the diaper 10 is repeatedly worn and taken off. In the sides 103 adjacent to the space 159 in the lateral direction X, the rear waist panel 30 comes into contact with the skin S, whereby body exudates may be prevented from spreading out from the space 159 in the lateral direction X. The front waist panel 20 and the crotch panel 40 of this diaper 10 may be those in the exemplary mode illustrated in FIG. 4.

<Measurement and Comparison of Contraction Amount>

In the present invention, the elastic contraction amounts of the elastic bands 1*a*, 1*b*, and 1*c* and other parts may be measured and compared in the following manner. For example, the middle part 44*b* of the inner elastic strip 44 in FIG. 4 and a component part of the diaper facing the middle part 44*b* in the thickness direction of the middle part 44*b* are compared with each other as follows. First of all, the diaper 10 in the stretched state, as a result of stretching the diaper 10 in the lateral direction X and the upper and lower direction Y until the gather disappears is prepared. In the diaper 10 in the stretched state, a straight line, for obtaining an entire length of a contraction amount measurement target range in the lateral direction X, is drawn on each of the middle part 44*b* and the part facing the middle part 44*b*. Then, a length (entire length) is $L_1$ measured on each straight line. Then, measurement samples are obtained by cutting away the middle part 44*b* and the part facing the middle part 44*b* from the diaper 10 in the stretched state. The measurement samples are placed on a flat surface to be contracted. A length $L_2$ of the straight line drawn on each of the contracted measurement samples is measured with the samples each held with a scale or the finger to be maintained in a linear form. An elastic contraction amount $L_3$ is obtained as a difference between the length $L_1$ and the length $L_2$. Thus, the elastic contraction amounts $L_3$ of the samples are compared with each other. The center part 44*b* and the part facing the center part 44*b* are joined to each other with hot-melt adhesive and thus may be difficult to cut away from the diaper 10 in the stretched state. In such an instance, the hot-melt adhesive may be dissolved with a toluene solution. The length $L_1$ and the length $L_2$ are preferably accurately measured in an order of 0.1 mm. When the straight line for measuring the entire length in the lateral direction X is difficult to draw, a length of one part over the entire length may be measured and the entire length may be derived from the length thus measured.

The invention claimed is:

1. A disposable absorbent wearing article having an upper and lower direction and a lateral direction crossing each other when the disposable absorbent wearing article is in a worn state, the disposable absorbent wearing article comprising:
   a front waist region defined by a front waist panel;
   a rear waist region defined by a rear waist panel;
   a crotch region positioned between the front and the rear waist regions and defined by a crotch panel,
   wherein
   the front waist region, the rear waist region and the crotch region each have a skin-facing surface and a clothing-facing surface respectively for facing a skin and clothing of a wearer in the worn state,
   an absorbent structure including an absorbent core material in the crotch panel extends in the front and the rear waist regions,
   at least one waist region of the front and the rear waist regions includes an elastic band forming a part of the skin-facing surface and having a middle part in the lateral direction elastically contracted in the lateral direction,
   in the at least one waist region, an elastic contraction amount of the middle part of the elastic band in the lateral direction is larger than an elastic contraction amount of a part facing the middle part without being joined to the middle part, in a thickness direction of the middle part in the lateral direction,
   in the core material in the at least one waist region, a deformation guide is formed extending in a direction to cross the elastic band and facilitating curving of the core material in the lateral direction,
   the at least one waist region includes a waist elastic area that extends along a top edge of the waist region and is capable of elastically contracting in the lateral direction, and has a part positioned more on a lower side than the waist elastic region folded in the upper and lower direction in an overlapping manner so that a Z-shaped folded part is formed, and
   in the Z-shaped folded part, both side parts positioned on both sides in the lateral direction are folded in an overlapping manner and joined to each other, a part between the both side parts is in a non-joined state, and a part of the waist elastic area forms the elastic band.

2. The wearing article according to claim 1, wherein the elastic band is formed of an elastic strip having both side ports in the lateral direction joined to the at least one waist region and having at least a lower part of the middle part not joined to the at least one waist region.

3. The wearing article according to claim 1, wherein the at least one waist region includes an outer sheet forming the clothing-facing surface, an inner sheet forming the skin-facing surface, and an elastic member provided between the outer sheet and the inner sheet and stretched in the lateral direction.

4. The wearing article according to claim 3, wherein in the at least one waist region, a non-elastic area is formed in the part facing the middle part.

5. The wearing article according to claim 1, wherein the deformation guide is at a position overlapping the elastic band in a planary view of the wearing article.

6. The wearing article according to claim 1, wherein the deformation guide is at a position not overlapping with the elastic band in a planary view of the wearing article.

7. The wearing article according to claim 1, wherein the elastic band is formed of a nonwoven fabric including elastic yarns, and the nonwoven fabric is in a state of being elastically stretched in the lateral direction at least in the middle part of the elastic band.

8. The wearing article according to claim 1, wherein the elastic band is formed of a nonwoven fabric to which a string-like or strip-like elastic members linearly extending in the lateral direction is contractibly attached.

9. The wearing article according to claim 1, wherein
a plurality of string-like or strip-like elastic members linearly extending in the lateral direction are contractibly attached to the at least one waist region while being arranged side by side along the upper and lower direction, and
the plurality of elastic members include an elastic member having an inner end facing a vertical center line that equally divides a length of the wearing article in the lateral direction.

10. The wearing article according to claim 9, wherein a length of a distance between the vertical center line and the inner end of at least one of the plurality of elastic members positioned in a lowermost part in the upper and lower direction is smaller than a length of a distance between the vertical center line and the inner end of one of the elastic members positioned more on an upper side than the at least one elastic member.

11. The wearing article according to claim 1, wherein the deformation guide is at least one slit or groove formed in the core material of the crotch panel and extends in the upper and lower direction.

12. The wearing article according to claim 11, wherein the at least one slit includes
a slit positioned on a vertical center line dividing equally a length of the wearing article in the lateral direction, and
slits formed symmetrically about the vertical center line.

13. The wearing article according to claim 11, wherein the at least one slit has both ends in the upper and lower direction formed in at least one of
an area between a front edge of the core material and a lateral center line of the wearing article and
an area between a rear edge of the core material and the lateral center line.

14. The wearing article according to claim 1, wherein the core material has at least one of a thickness and a density varying between parts adjacent to the deformation guide in the lateral direction and the deformation guide.

* * * * *